(12) United States Patent
Wang et al.

(10) Patent No.: US 10,617,283 B2
(45) Date of Patent: Apr. 14, 2020

(54) SELF-LOCKING ANGLE ADJUSTMENT MECHANISM FOR ENDOSCOPE

(71) Applicant: YOUCARE TECHNOLOGY CO., LTD. (WUHAN), Wuhan, Hubei (CN)

(72) Inventors: Shaogang Wang, Hubei (CN); Jianxing Li, Beijing (CN); Xiaolin Guo, Hubei (CN); Jian Huang, Guangdong (CN); Xu Zhang, Beijing (CN); Jihong Liu, Hubei (CN); Yiran Huang, Shanghai (CN); Lin Qi, Hunan (CN); Xiuheng Liu, Hubei (CN); Xiaoping Zhang, Hubei (CN); Tongzu Liu, Hubei (CN); Zhangqun Ye, Hubei (CN); Kunjie Wang, Sichuan (CN); Xiao Yu, Hubei (CN); Qi Chen, Shanghai (CN); Lei Song, Beijing (CN); Yaohui Wu, Hubei (CN); Yeyun Mao, Hubei (CN); Ying Li, Hubei (CN); Xuecheng Hu, Hubei (CN); Gang Long, Hubei (CN)

(73) Assignee: YOUCARE TECHNOLOGY CO., LTD. (WUHAN), Wuhan, Hubei (CN)

(*) Notice: Subject to any disclaimer, the term of this patent is extended or adjusted under 35 U.S.C. 154(b) by 367 days.

(21) Appl. No.: 15/533,326

(22) PCT Filed: Jun. 2, 2015

(86) PCT No.: PCT/CN2015/080555
§ 371 (c)(1),
(2) Date: Jun. 5, 2017

(87) PCT Pub. No.: WO2016/192034
PCT Pub. Date: Dec. 8, 2016

(65) Prior Publication Data
US 2017/0325659 A1 Nov. 16, 2017

(51) Int. Cl.
 A61B 1/005 (2006.01)
 A61B 1/00 (2006.01)
 A61M 25/01 (2006.01)
(52) U.S. Cl.
 CPC .......... A61B 1/0052 (2013.01); A61B 1/0057 (2013.01); A61B 1/00066 (2013.01); A61M 25/0136 (2013.01)
(58) Field of Classification Search
 CPC .................. A61B 1/00066; A61B 1/0052
 (Continued)

(56) References Cited

U.S. PATENT DOCUMENTS

2013/0158379 A1* 6/2013 Selkee ................ A61B 1/0052
600/373

* cited by examiner

*Primary Examiner* — Aaron B Fairchild

(57) ABSTRACT

A self-locking angle adjustment mechanism for an endoscope includes: an endoscope angle adjustment steel wire (5), a rotation handle (2), an endoscope handle (3) and a self-locking rotation device, wherein: an outer conical surface is provided at an external surface of the rotation shaft (7), a conical cylinder is sleeved onto the outer conical surface; a spring (14), which can drive the rotation shaft to move towards a direction of the conical cylinder or drive the conical cylinder to move towards a direction of the rotation shaft, and can force the inner conical surface to closely fit with the outer conical surface for self-locking, is located along an axial direction of the rotation shaft or conical cylinder. Through the present invention, the flexible sheath is locked stepless at any position, meeting free positioning requirement of endoscope during surgeries, reducing labor strength during surgeries, avoiding patient injuries caused by misoperations.

13 Claims, 2 Drawing Sheets

(58) Field of Classification Search
USPC .................................................. 600/146, 148
See application file for complete search history.

SELF-LOCKING ANGLE ADJUSTMENT MECHANISM FOR ENDOSCOPE

CROSS REFERENCE OF RELATED APPLICATION

This is a U.S. National Stage under 35 U.S.C 371 of the International Application PCT/CN2015/080555, filed Jun. 2, 2015.

BACKGROUND OF THE PRESENT INVENTION

Field of Invention

The present invention relates to medical devices, and more particularly to a self-locking angle adjustment mechanism for an endoscope.

Description of Related Arts

Clinically, the endoscopic treatment is the most commonly used minimally invasive treatment, which has less damage to patients. At present, the flexible endoscope is usually controlled by the scissors handle and the steering steel wire for bending and steering thereof, the operation precision is not high, and the control of the angle is not accurate enough; during the operation, with the operation of medical personnel, the angle adjustment device is repeatedly used, therefore, the angle of the steering steel wire is more or less biased, thereby the accuracy of the operation is not high; furthermore, the repeated use of the steering steel wire is able to cause the steel wire to twist and bend within the endoscope, leading to a low angle adjustment sensitivity. There is also a push-pull handle. Their common feature is the ability to achieve the purpose of turning the front end of the flexible endoscope, but both fails to real-time position and lock, and the doctor in the operation process needs to maintain a certain holding position for a long time. Surgical operation always consumes a lot of physical strength of doctors, so this operation increases their burden. In case of a negligent change in the hand grip position, the turning angle of the front end will be altered, which may bring great security risks to the operation due to such a small change.

Minimally invasive operation has a high demand for the stability and flexibility of the endoscopic device to avoid repeated angle adjustment and positioning in the patient's body, and it is urgent for the endoscopic device with the high safety and high efficiency to meet the clinical diagnosis and treatment requirements.

SUMMARY OF THE PRESENT INVENTION

An object of the present invention is to overcome the drawbacks of the background arts described above and to provide an angle adjustment mechanism for an endoscope, which has characteristics of simple operation and real-time locking, thereby greatly improving the surgical safety.

Accordingly, in order to accomplish the above object, the present invention adopts technical solutions as follows.

A self-locking angle adjustment mechanism for an endoscope, which comprises: an endoscope angle adjustment steel wire, a rotation handle, an endoscope handle and a self-locking rotation device located within the endoscope handle, wherein:

an inner end of the endoscope angle adjustment steel wire is located within the endoscope handle;

the self-locking rotation device comprises a rotation shaft, and a spring; the rotation shaft is located within the endoscope handle; an outer conical surface is provided at an external surface of the rotation shaft, a conical cylinder, which matches the outer conical surface, is sleeved to the outer conical surface, an inner wall of the conical cylinder is an inner conical surface, and the inner conical surface corresponds to the outer conical surface; the spring, which is capable of driving the rotation shaft to move towards a direction of the conical cylinder or driving the conical cylinder to move towards a direction of the rotation shaft, and is capable of forcing the inner conical surface to closely fit with the outer conical surface for self-locking, is located along an axial direction of the rotation shaft or the conical cylinder; the inner end of the endoscope angle adjustment steel wire is fixed to the rotation shaft, and the rotation handle is connected with the rotation shaft.

Preferably, two ends of the rotation shaft are respectively located within two positioning holes in two opposite inner walls of the endoscope handle; the conical cylinder is inserted into one of the two positioning holes in one of the inner walls of the endoscope handle and is coaxially aligned with one of the positioning holes; one end of the conical cylinder where the conical cylinder is opposite to the outer conical surface has an internal conical face with large exterior and small interior; the spring is sleeved over an external surface of the rotation shaft.

Preferably, a boss is located at the external surface of the rotation shaft, and the outer conical surface is provided on the boss; one end of the spring is placed against an end surface of the boss.

Preferably, the conical cylinder is inserted into the inner wall at one side of the endoscope handle, and on the end of the conical cylinder with its back to the internal conical face with large exterior and small interior, there is a round hole.

Preferably, two ends of the rotation shaft are respectively located in the positioning holes in two opposite inner walls of the endoscope handle, and the rotation shaft is axially positioned in the positioning holes; one end of the conical cylinder has the inner conical surface with large exterior and small interior which is correspondingly sleeved onto the outer conical surface of the rotation shaft, another end thereof has a round hole which is sleeved onto the rotation shaft which is located aside of the outer conical surface, and an external surface of the rotation shaft located aside of the outer conical surface is cylindrical; the spring is sleeved over the external surface of the rotation shaft, one end of the spring is placed against the end of the conical cylinder having the round hole along the axial direction thereof, and another end of the spring is placed against one of the inner walls of the endoscope handle.

Preferably, the spring contacts with an inner side of the endoscope handle through a planar bearing and a spring adjustment nut, the spring adjustment nut has external screw threads on an external surface thereof, the inner wall of the endoscope handle has internal threaded holes, the external screw threads of the spring adjustment nut are engaged with the internal threaded holes, and the planar bearing is located on the rotation shaft between the spring and the spring adjustment nut.

Preferably, the inner end of the endoscope angle adjustment steel wire is fixed to the rotation shaft through a steel wire wheel, the steel wire wheel is sleeved onto and fixed to the rotation shaft, the inner end of the endoscope angle adjustment steel wire is fixed and wound to a positioning groove which is provided on an external circle of the steel wire wheel.

Preferably, the two ends of the rotation shaft respectively protrude through the two inner walls of the endoscope handle; the rotation handle is U-shaped, and two ends of the rotation handle are respectively fixed with the two ends of the rotation shaft which are located outside the endoscope handle.

Preferably, the two ends of the rotation handle are respectively fixed with two ends of the rotation shaft through connecting pieces; the two ends of the rotation shaft which are located outside the endoscope handle respectively have concave step faces, every connecting piece has an inner hole, which makes an interference fit with the step face at the two ends of the rotation shaft, and the external surface of the connecting pieces makes an interference fit with the inner holes at the two ends of the rotation handle.

Preferably, the axial direction of the rotation shaft is vertical to an axis of the endoscope handle.

The present invention has advantages of reliable positioning limit, simple structure and convenient machining and assembly, and more particularly, the present invention adopts the specific self-locking angle adjustment mechanism; through adjusting an engagement depth of the spring adjustment nut, a compression degree and a restoring force of the spring are adjusted, so as to closely engage the outer conical surface on the rotation shaft with the inner conical surface in the conical cylinder, for balancing a friction force therebetween and the restoring force of the spring, thereby achieving self-locking. Through the mechanism mentioned above, the flexible sheath is able to be locked stepless at any position, so as to meet free positioning requirement of the endoscope during the surgery, and reduce labor strength during the surgery, thereby avoiding patient injury caused by error operations.

The present invention is designed according to ergonomics, to meet requirements of operating the endoscope with one hand by the doctor, so that an angle of the rotation handle being operated is corresponding to a flexible sheath bending angle, and during surgery, the doctor is able to clearly perceive and operate the sheath to bend, thereby reaching a required bending angle.

Figure 1:
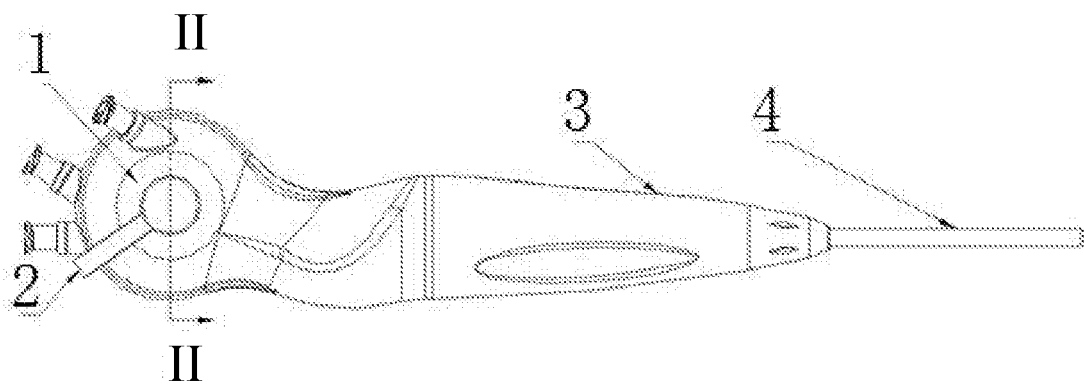
FIG. 1 is a front view of a self-locking adjustment mechanism for an endoscope according to a preferred embodiment of the present invention.

In the drawings, 1: locking cover plate; 2: rotation handle; 3: endoscope handle; 4: flexible sheath; 5: adjustment steel wire; 6: rotation shaft core; 7: rotation shaft; 8: small side cover; 9: spring adjustment nut; 10: side cover; 11: steel wire wheel; 12: planar bearing; 13: pin; 14: spring; 15: conical cylinder; 16: inner conical surface; 17: outer conical surface.

DETAILED DESCRIPTION OF THE PREFERRED EMBODIMENT

The present invention is explained in detail with accompanying drawings as follows, which are not the limitation to the present invention and are only the examples.

Embodiment 1

Figure 2:
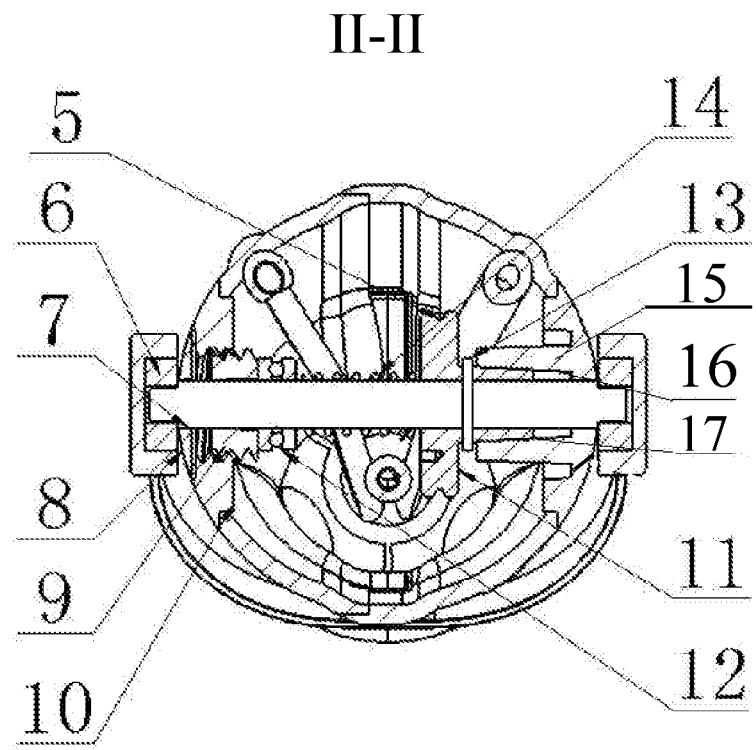
FIG. 2 is a sectional view of FIG. 1 along an II-II direction.
Figure 3:
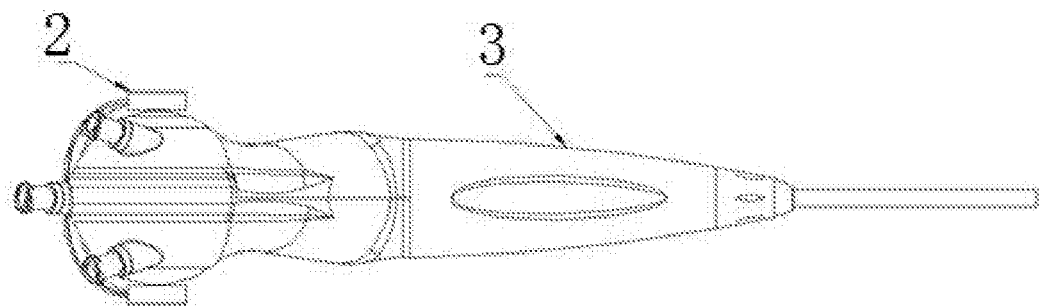
FIG. 3 is a top view of the self-locking adjustment mechanism for the endoscope shown in FIG. 1.
Figure 4:
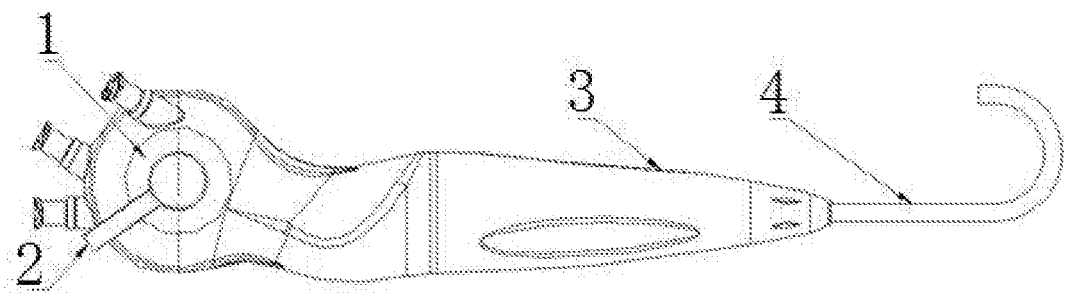
FIG. 4 is a working state diagram of the self-locking adjustment mechanism for the endoscope according to the preferred embodiment of the present invention.
Figure 5:
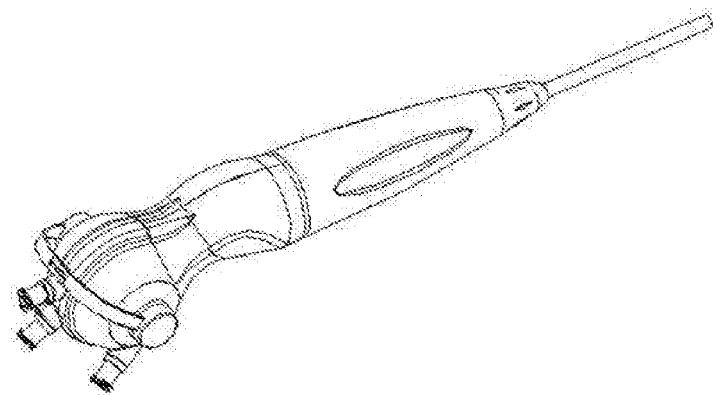
FIG. 5 is a three-dimensionally schematic view of the self-locking adjustment mechanism for the endoscope according to the preferred embodiment of the present invention.

Referring to FIGS. 1-3, a self-locking angle adjustment mechanism for an endoscope according to a first preferred embodiment of the present invention is illustrated, which comprises: an endoscope angle adjustment steel wire 5, a rotation handle 2, an endoscope handle 3 and a self-locking rotation device located within the endoscope handle 3. An inner end of the endoscope angle adjustment steel wire 5 is located within the endoscope handle 3; the self-locking rotation device comprises a rotation shaft 7, a spring 14 and a rotation handle 2; the rotation shaft 7 is located within the endoscope handle 3 and supported by positioning holes in two opposite inner walls of the endoscope handle 3, the positioning holes are provided in a locking cover plate 1, and the locking cover plate 1 is inserted and fixed to the inner wall of the endoscope handle 3; two ends of the rotation shaft are respectively located in the positioning holes in the locking cover plate 1 at the two opposite inner walls of the endoscope handle 3, and the rotation shaft has a gap along an axial direction thereof in each of the positioning holes.

An outer conical surface 17 and a steel wire wheel 11, both of which are coaxially aligned with the rotation shaft, are located at an external surface of the rotation shaft 7, the outer conical surface is provided outside of the steel wire wheel 11 and integrated with the steel wire wheel 11, and the inner end of the endoscope angle adjustment steel wire 5 is fixed to and wound around a positioning groove which is provided at an external circle of the steel wire wheel 11. The steel wire wheel 11 and the outer conical surface are sleeved onto the rotation shaft and fixed to the rotation shaft through a pin 13, as shown in FIG. 2.

A conical cylinder 15, which matches the outer conical surface, is sleeved onto the outer conical surface, an inner wall of the conical cylinder is an inner conical surface 16, and one end of the conical cylinder opposite to the outer conical surface is the inner conical surface which is large in exterior and small in interior; the inner conical surface is corresponding to the outer conical surface; the conical cylinder is integrated with the locking cover plate 1 on one of the inner walls of the endoscope handle 3, and an end of the conical cylinder with its back to the inner conical surface with large exterior and small interior, is integrated with the locking cover plate 1 and coaxially aligned with the positioning holes in the locking cover plate 1, as shown in FIG. 2.

The spring 14, which is capable of driving the rotation shaft to move towards a direction of the conical cylinder and forcing the inner conical surface to closely fit with the outer conical surface, is located at the axial direction of the rotation shaft; the spring 14 is sleeved over an external surface of the rotation shaft, one end of the spring is placed against an inner wall of the locking cover plate 1 at one side of the endoscope handle 3, and another end of the spring is placed against an inner end surface of the steel wire wheel 11 along an axial direction thereof. The spring 14 contacts with the inner wall of the locking cover plate 1 through the planar bearing 12 and the spring adjustment nut 9 in sequence, the spring adjustment nut 9 has outer screw threads on an external surface thereof, the inner wall of the locking cover plate 1 has inner threaded holes thereon, and the outer screw threads of the spring adjustment nut 9 are engaged with the inner threaded holes; the planar bearing 12 is located on the rotation shaft between the spring 14 and the spring adjustment nut 9, as shown in FIG. 2.

The two ends of the rotation shaft respectively protrude through the locking cover plate 1 on the two inner walls of the endoscope handle 3; the rotation handle 2 is U-shaped, two ends of the rotation handle are respectively fixed with the two ends of the rotation shaft through connecting pieces 6; the two ends of the rotation shaft which are located outside the endoscope handle 3 respectively have concave step faces, every connecting piece 6 has an inner hole, which makes an interference fit with the step face at the two ends of the rotation shaft, and the external surface of the connecting pieces 6 makes an interference fit with the inner holes at the two ends of the rotation handle 2. The axial direction of the rotation shaft 7 is vertical to an axis of the endoscope handle 3, as shown in FIG. 2.

The connecting piece 16 is able to be made of plastic.

While assembling, firstly, the steel wire wheel 11 and the outer conical surface are sleeved and fixed to the rotation shaft 7 through the pin 13; and then one end of the adjustment steel wire 5 is fixed and wound to the positioning groove on the external circle of the steel wire wheel 11; and then the spring 14, the planar bearing 12 and the spring adjustment nut 9 are installed to the rotation shaft 7 in sequence, the rotation shaft is installed in the positioning holes; through the gaps between the rotation shaft and the positioning holes, the inner conical surface of the conical cylinder is corresponding to and slightly contacts the outer conical surface fixed on the rotation shaft (contacts without pressure); through adjusting an engagement depth of the spring adjustment nut 9 and the locking cover plate 1, a compression degree and a restoring force of the spring 14 are adjusted, so as to closely engage the above mentioned outer conical surface with the inner conical surface (namely, the outer conical surface contacts the inner conical surface with pressure), for balancing a friction force therebetween and the restoring force of the spring 14, thereby achieving self-locking. As a result, while operating the rotation handle 2 to drive the rotation shaft 7 to rotate, not only easy driving but also no rebound is achieved. Finally, the rotation handle 2 is installed and fixed.

Embodiment 2

The second embodiment has a similar structure with the first embodiment (not shown in the drawings). Differences therebetween are as follows. The steel wire wheel 11 and the outer conical surface are independent from each other. The outer conical surface is provided on a surface of a boss which is located at an external surface of the rotation shaft; the boss is a circular sleeve coaxially aligned with the rotation shaft, which is able to be integrated with the rotation shaft, and is also able to be an independent component to be sleeved onto the rotation shaft and fixed to the rotation shaft through the pin. The outer conical surface is provided on the boss; the steel wire wheel 11 is coaxially fixed to the rotation shaft which is located between the outer conical surface and an inner wall at one side of the endoscope handle 3, through splines or pin shafts. A diameter of the outer conical surface is gradually decreased along the direction of the spring.

The conical cylinder is an independent component, one end thereof is the inner conical surface with large exterior and small interior which is correspondingly sleeved onto the outer conical surface of the rotation shaft, another end thereof is a round hole which is sleeved onto the rotation shaft located aside of the outer conical surface, an external surface of the rotation shaft located aside of the outer conical surface is cylindrical, and the cylindrical shape matches the round hole at another end of the conical cylinder; the spring 14 is sleeved over the external surface of the rotation shaft, of which one end is placed against a round hole end of the conical cylinder along the axial direction thereof, and another end adopts a same structure as the first embodiment to be placed against an inner wall at one side of the endoscope handle 3.

In the present invention, through operating the rotation handle 2, the rotation shaft 7 is driven to rotate, and simultaneously, the steel wire wheel 5 on the rotation shaft 7 is consequently driven, pulling the adjustment steel wire 5, which is coaxially fixed with the flexible sheath 4. Through the mechanism mentioned above, the flexible sheath is able to be locked stepless at any position, and also, the endoscope is able to be operated with one hand, thereby reducing burdens on doctors.

The endoscope provided by the present invention has excellent reliability, accurate positioning, simple structure and convenient assembly.

Other components and connection structures of the endoscope are prior arts, and are not specifically described herein.

The following is a brief summary of the several conventional applications of the present invention.

1. Urological application: The self-locking angle adjustment mechanism provided by the present invention is able to be used for ureteroscopes, and optimize the current cystoscopes and percutaneous nephroscopes, effectively reduce doctors' surgical strength, and increase the surgical precision. Furthermore, it is also able to be applied to the treatment of kidney stones, bladder stones, renal cysts, and renal tumors.

2. Application in neurosurgery: The self-locking angle adjustment mechanism provided by the present invention is able to ensure a safe and reliable operation, and be widely used for the treatment of hydrocephalus, intraventricular disease, skull base surgery, pituitary tumor, aneurysm, intracranial hematoma, and subdural hematoma, and in particular, separated subdural hematoma and endoscopic percutaneous discectomy, and even for brain parenchyma tumor biopsy and small tumor resection, trigeminal microvascular decompression and vestibular nerve section and so on.

3. Application in gynecology: The self-locking angle adjustment mechanism provided by the present invention is able to be used in the falloposcope, optimizing the present hysteroscope, laparoscope and colposcope; and it is also able to be used for clinical patient with precancerous cervical lesions or suspicious cervical cancer, person with abnormal cells found in anti-cancer pictures, and cervical lesions after follow-up treatment, so as to understand the treatment effect whether recurrence or new lesions occur, abnormal uterine bleeding, uterine fibroids, polyps and endometrial cancer, abnormal ultrasound sound and video findings, infertility and family planning complications, hormone replacement and application of tamoxifen induced endometrial physiological or special changes, previous IVF (in vitro fertilization) failing patients; to replace hysteroscopy to check endometrial conditions, habitual abortion, to see whether the uterine cavity is normal, metrosynizesis, foreign bodies in uterine cavity, and to cut benign gynecologic tumors, diagnose and treat exfetation, treat oophoritic cyst, strip pelvic adhesions, burn endometriosis and ligature oviduct and so on.

4. Application in general surgery: The self-locking angle adjustment mechanism provided by the present invention is able to be used in laparoscopes including various optimized laparoscopes such as the HD type and the ultrafine type, which is applicable not only to external open channels but also to various natural orifices. Also, it is able to be used for surgical treatment of liver, biliary tract, pancreatic, gastrointestinal, anorectal, and vascular diseases, thyroid and breast tumors and trauma and other diseases.

In addition, the self-locking angle adjustment mechanism provided by the present invention is also able to be used in departments of digestive medicine, pancreas surgery, vascular surgery and respiratory department.

The foregoing is intended to be illustrative of the preferred embodiments of the present invention and is not intended to limit the structure of the present invention in any way. Any simple modifications, equivalent changes and modifications to the above embodiments in accordance with the technical essence of the present invention are within the scope of the present invention.

What is claimed is:

1. A self-locking angle adjustment mechanism for an endoscope, which comprises: an endoscope angle adjustment steel wire, a rotation handle, an endoscope handle and a self-locking rotation device located within the endoscope handle, wherein:
   an inner end of the endoscope angle adjustment steel wire is located within the endoscope handle;
   the self-locking rotation device comprises a rotation shaft, a spring, and the rotation handle;
   the rotation shaft is located within the endoscope handle;
   an outer conical surface is provided at an external surface of the rotation shaft;
   a conical cylinder, which matches the outer conical surface, is sleeved onto the outer conical surface, an inner wall of the conical cylinder is an inner conical surface, and the inner conical surface corresponds to the outer conical surface;
   the spring is located along an axial direction of the rotation shaft or the conical cylinder, and the spring is capable of driving the rotation shaft to move towards a direction of the conical cylinder or driving the conical cylinder to move towards a direction of the rotation shaft, and is capable of forcing the inner conical surface to closely fit with the outer conical surface for self-locking;
   the inner end of the endoscope angle adjustment steel wire is fixed to the rotation shaft, and the rotation handle is connected with the rotation shaft;
   two ends of the rotation shaft are respectively located within two positioning holes in two opposite inner walls of the endoscope handle;
   the conical cylinder is inserted into one of the two positioning holes in one of the inner walls of the endoscope handle and is coaxially aligned with the one of the two positioning holes;
   one end of the conical cylinder where the conical cylinder is opposite to the outer conical surface has the internal conical face with large exterior and small interior;
   the spring is sleeved over an external surface of the rotation shaft.

2. The self-locking angle adjustment mechanism for the endoscope, as recited in claim 1, wherein: a boss is located at the external surface of the rotation shaft, and the outer conical surface is provided on the boss; one end of the spring is placed against an end surface of the boss.

3. The self-locking angle adjustment mechanism for the endoscope, as recited in claim 2, wherein:
   the spring contacts with an inner side of the endoscope handle through a planar bearing and a spring adjustment nut;
   the spring adjustment nut has external screw threads on an external surface thereof, the inner wall of the endoscope handle has internal threaded holes, the external screw threads of the spring adjustment nut are engaged with the internal threaded holes;
   the planar bearing is located on the rotation shaft between the spring and the spring adjustment nut.

4. The self-locking angle adjustment mechanism for the endoscope, as recited in claim 3, wherein:
   the inner end of the endoscope angle adjustment steel wire is fixed to the rotation shaft through a steel wire wheel;
   the steel wire wheel is sleeved onto and fixed to the rotation shaft;
   the inner end of the endoscope angle adjustment steel wire is fixed and wound to a positioning groove which is provided on an external circle of the steel wire wheel.

5. The self-locking angle adjustment mechanism for the endoscope, as recited in claim 1, wherein: the conical cylinder is inserted into the inner wall at one side of the endoscope handle; an end of the conical cylinder with its back to the internal conical face with large exterior and small interior, has a round hole.

6. The self-locking angle adjustment mechanism for the endoscope, as recited in claim 5, wherein:
   the spring contacts with an inner side of the endoscope handle through a planar bearing and a spring adjustment nut;
   the spring adjustment nut has external screw threads on an external surface thereof, the inner wall of the endoscope handle has internal threaded holes, the external screw threads of the spring adjustment nut are engaged with the internal threaded holes;
   the planar bearing is located on the rotation shaft between the spring and the spring adjustment nut.

7. The self-locking angle adjustment mechanism for the endoscope, as recited in claim 6, wherein:
   the inner end of the endoscope angle adjustment steel wire is fixed to the rotation shaft through a steel wire wheel;
   the steel wire wheel is sleeved onto and fixed to the rotation shaft;
   the inner end of the endoscope angle adjustment steel wire is fixed and wound to a positioning groove which is provided on an external circle of the steel wire wheel.

8. The self-locking angle adjustment mechanism for the endoscope, as recited in claim 6, wherein:
   the two ends of the rotation shaft respectively protrude through the two inner walls of the endoscope handle;
   the rotation handle is U-shaped, and two ends of the rotation handle are respectively fixed with the two ends of the rotation shaft which are located outside the endoscope handle.

9. The self-locking angle adjustment mechanism for the endoscope, as recited in claim 8, wherein: the two ends of the rotation handle are respectively fixed with two ends of the rotation shaft through connecting pieces;

the two ends of the rotation shaft which are located outside the endoscope handle respectively have concave step faces;

every connecting piece has an inner hole, the inner hole makes an interference fit with the step face at the two ends of the rotation shaft, and the external surface of the connecting pieces makes an interference fit with the inner holes at the two ends of the rotation handle.

10. The self-locking angle adjustment mechanism for the endoscope, as recited in claim 1, wherein:

the spring contacts with an inner side of the endoscope handle through a planar bearing and a spring adjustment nut;

the spring adjustment nut has external screw threads on an external surface thereof, the inner wall of the endoscope handle has internal threaded holes, the external screw threads of the spring adjustment nut are engaged with the internal threaded holes;

the planar bearing is located on the rotation shaft between the spring and the spring adjustment nut.

11. The self-locking angle adjustment mechanism for the endoscope, as recited in claim 10, wherein:

the inner end of the endoscope angle adjustment steel wire is fixed to the rotation shaft through a steel wire wheel;

the steel wire wheel is sleeved onto and fixed to the rotation shaft;

the inner end of the endoscope angle adjustment steel wire is fixed and wound to a positioning groove which is provided on an external circle of the steel wire wheel.

12. The self-locking angle adjustment mechanism for the endoscope, as recited in claim 10, wherein:

the two ends of the rotation shaft respectively protrude through the two inner walls of the endoscope handle;

the rotation handle is U-shaped, and two ends of the rotation handle are respectively fixed with the two ends of the rotation shaft which are located outside the endoscope handle.

13. The self-locking angle adjustment mechanism for the endoscope, as recited in claim 10, wherein: the axial direction of the rotation shaft is vertical to an axis of the endoscope handle.

* * * * *